United States Patent [19]

Lavanish

[11] 4,268,675
[45] * May 19, 1981

[54] 3-[5-[1-(DIHALOPHENOXY)ALKYL, ALKYNYL, ALKENYL, OR HALOALKYL]-1,3,4-THIADIAZOL-2-yl]-4-HYDROXY-1-METHYL-2-IMIDAZOLIDINONES

[75] Inventor: Jerome M. Lavanish, Akron, Ohio

[73] Assignee: PPG Industries, Inc., Pittsburgh, Pa.

[*] Notice: The portion of the term of this patent subsequent to Aug. 19, 1997, has been disclaimed.

[21] Appl. No.: 55,228

[22] Filed: Jul. 6, 1979

[51] Int. Cl.³ .................. A01N 43/82; C07D 285/12; C07D 417/02; C07D 417/04
[52] U.S. Cl. ...................................... 548/137; 71/90; 548/138; 548/139; 548/140; 562/472
[58] Field of Search ........................................ 548/137

[56] References Cited

U.S. PATENT DOCUMENTS

| 3,758,492 | 9/1973 | Metzger et al. | 548/137 |
|---|---|---|---|
| 3,759,939 | 9/1973 | Metzger et al. | 548/137 |
| 3,784,555 | 1/1974 | Cebalo | 548/138 |
| 3,849,432 | 11/1974 | Metzger et al. | 548/137 |
| 3,901,904 | 8/1975 | Krenzer | 548/137 |
| 3,901,905 | 8/1975 | Krenzer | 548/137 |
| 3,904,640 | 9/1975 | Krenzer | 548/137 |
| 3,920,674 | 11/1975 | Krenzer | 548/137 |
| 3,925,402 | 12/1975 | Krenzer | 548/137 |
| 3,964,895 | 6/1976 | Krenzer | 548/137 |
| 4,012,223 | 3/1977 | Krenzer | 548/137 |
| 4,023,957 | 5/1977 | Krenzer | 548/137 |
| 4,028,375 | 6/1977 | Krenzer | 548/137 |
| 4,036,848 | 7/1977 | Krenzer | 548/137 |
| 4,052,191 | 10/1977 | Krenzer | 548/137 |
| 4,093,443 | 6/1978 | Krenzer | 548/137 |

Primary Examiner—Alton D. Rollins
Attorney, Agent, or Firm—Edward J. Whitfield; Robert J. Grassi

[57] ABSTRACT

The disclosed compounds, such as 3-[5-[1-(3,5-dichlorophenoxy) ethyl]-1,3,4-thiadiazol-2-yl]-4-hydroxy-1-methyl-2-imidazolidinone, are useful for preemergence control of weeds, such as jimsonweed.

20 Claims, No Drawings

3-[5-[1-(DIHALOPHENOXY)ALKYL, ALKYNYL, ALKENYL, OR HALOALKYL]-1,3,4-THIADIAZOL-2-YL]-4-HYDROXY-1-METHYL-2-IMIDAZOLIDINONES

BACKGROUND OF THE INVENTION

1. FIELD OF THE INVENTION

The invention relates to substituted 1,3,4-thiadiazol-2-yl-4-hydroxy-1-methyl-2-imidazolidinone, particularly to the 3-[5-[1-dihalophenoxyalkyl, -alkynyl, -alkenyl, -or haloalkyl substituted)]-1,3,4-thiadiazol-2-yl]-4-hydroxy-1-methyl-2-imidazolidinone compounds.

2. DESCRIPTION OF THE PRIOR ART

Imidazolidinones, as a class, are described in patents and chemical literature; none of which, however, teaches or discloses the novel herbicidal compounds described herein and their use to control the weeds described herein.

SUMMARY OF THE INVENTION

The invention described herein concerns compounds graphically represented by Formula I.

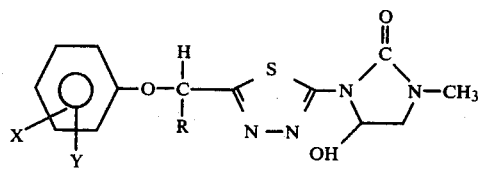

wherein:
X is chlorine, bromine, fluorine, or iodine,
Y is chlorine, bromine, fluorine, or iodine, and;
R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 2-bromoethyl; the intermediates graphically represented by Formulas III, IV and V,

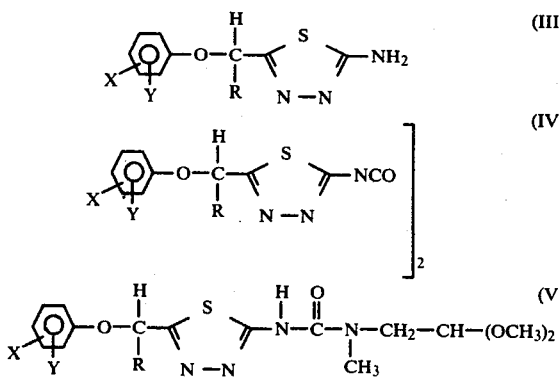

wherein: X, Y, and R are defined as herein, as well as the process for making compounds of the described formulas. The compounds of Formula I are particularly useful for controlling weeds preemergence and are selective to other weeds postemergence; especially the compounds where X and Y are chlorine and R is methyl. For example, the compound in which X and Y are chlorine located at the 3, 5 positions and R is methyl, is useful for controlling teaweed, jimsonweed, mustard, crabgrass, yellow foxtail, johnsongrass, velvetleaf, wild oats and morningglory at preemergence rates of ten pounds per acre.

DESCRIPTION OF THE PREFERRED EMBODIMENT

The novel agriculturally useful compounds described herein may be graphically represented by Formula I.

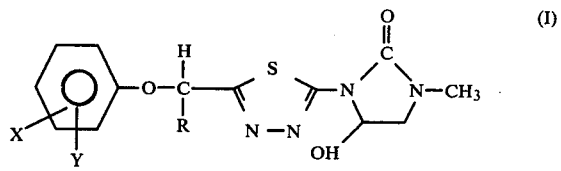

wherein:
X is chlorine, bromine, fluorine, or iodine
Y is chlorine, bromine, fluorine, or iodine, and
R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl and bromoethyl.

Examples of compounds represented by Formula I are:

3-[5-[1-(2,3-dichlorophenoxy)ethyl]-1,3,4-thiadiazol-2l-yl]-4-hydroxy-1-methyl-2-imidazolidinone.

3-[5-[1-(2,4-dichlorophenoxy)-2-bromoethyl]-1,3,4-thiadiazol-2-yl]-4-hydroxy-1-methyl-2-imidazolidinone.

3-[5-[1-(2,5-difluorophenoxy)-2-bromoethyl]-1,3,4-thiadiazol-2-yl]-4-hydroxy-1-methyl-2-imidazolidinone.

3-[5-[1-(2,6-diiodophenoxy)-3-chloropropyl]-1,3,4-thiadiazol-2-yl]-4-hydroxy-1-methyl-2-imidazolidinone.

3-[5-[1-(3,4-dichlorophenoxy)-3-bromopropyl]-1,3,4-thiadiazol-2-yl]-4-hydroxy-1-methyl-2-imidazolidinone.

3-[5-[1-(3,5-dibromophenoxy)-2-propynyl]-1,3,4-thiadiazol-2-yl]-4-hydroxy-1-methyl-2-imidazolidinone.

3-[5-[1-(2,4-difluorophenoxy-2-butynyl]-1,3,4-thiadiazol-2-yl]-4-hydroxy-1-methyl-2-imidazolidinone.

3-[5-[1-(2,3-diiodophenoxy)-3-butynyl]-1,3,4-thiadiazol-2-yl]-4-hydroxy-1-methyl-2-imidazolidinone.

3-[5-[1-(2,5-dichlorophenoxy)-2-propenyl]-1,3,4-thiadiazol-2-yl]-4-hydroxy-1-methyl-2-imidazolidinone.

3-[5-[1-(2,6-dibromopheonxy)-2-butenyl]-1,3,4-thiadiazol-2-yl]-4-hydroxy-1-methyl-2-imidazolidinone.

3-[5-[1-(3,4-difluorophenoxy)-2-chloroethyl]-1,3,4-thiadiazol-2-yl]-4-hydroxy-1-methyl-2-imidazolidinone.

3-[5-[1-(3,5-diiodophenoxy)-2-bromoethyl]-1,3,4-thiadiazol-2-yl]-4-hydroxy-1-methyl-2-imidazolidinone.

3-[5-[1-(2,3-dichlorophenoxy)-3-chloropropyl]-1-,3,4-thiadiazol-2-yl]-4-hydroxy-1-methyl-2-imidazolidinone.

3-[5-[1-(2,4-dibromophenoxy)-3-bromopropyl]-1,3,4-thiadiazol-2-yl]-4-hydroxy-1-methyl-2-imidazolidinone.

3-[5-[1-(2,5-difluorophenoxy)-3-butenyl]-1,3,4-thiadiazol-2-yl]-4-hydroxy-1-methyl-2-imidazolidinone.

3-[5-[1-(2,6-diiodophenoxy)-1-pentenyl]-1,3,4-thiadiazol-2-yl]-4-hydroxy-1-methyl-2-imidazolidinone.

3-[5-[1-(3,4-dichlorophenoxy)-1-(3-methylbutyl)]-1,3,4-thiadiazol-2-yl]-4-hydroxy-1-methyl-2-imidazolidinone.

3-[5-[1-(3,5-dibromophenoxy)-2-(2-methylbutyl)]-1,3,4-thiadiazol-2-yl]-4-hydroxy-1-methyl-2-imidazolidinone.

3-[5-[1-82,3-difluorophenoxy)-1-(2,2-dimethylpropyl)]-1,3,4-thiadiazol-2-yl]-4-hydroxy-1-methyl-2-imidazolidinone.

3-[5-[1(2,4-diiodophenoxy)-1-butyl]-1,3,4-thiadiazol-2-yl]-4-hydroxy-1-methyl-2-imidazolidinone.

3-[5-[1-(2,5-dichlorophenoxy)-2-methylpropyl]-1,3,4-thiadiazol-2-yl]-4-hydroxy-1-methyl-2-imidazolidinone.

3-[5-[1-(2,6-dibromophenoxy)propyl]-1,3,4-thiadiazol-2-yl]-4-hydroxy-1-methyl-2-imidazolidinone.

Although all of the compounds described herein are useful for the purpose described herein, some compounds are more useful than others. Compounds in which R is an alkynyl, are of a general utility, while compounds in which R is an alkenyl, are of better utility. Compounds in which R is a haloalkyl described herein are of high utility and of these, the preferred compounds are those in which R is chloromethyl or bromomethyl. Compounds in which R is an alkyl described herein, are highly preferred and especially are compounds in which the alkyl is methyl, ethyl, or propyl but methyl is the most preferred alkyl. X and Y are preferably chlorine or bromine, but chlorine is most preferred. The preferred positions of X and Y are at the 2, 4 positions, 3, 4 positions, and 3, 5 positions, and the 3, 5 positions are the most preferred positions. The following compounds are the most preferred: 3-[5-[1-(2,4-dichlorophenoxy)ethyl]-1,3,4-thiadiazol-2-yl]-4-hydroxy-1-methyl-2-imidazolidinone, 3-[5-[1-(3,5-dichlorophenoxy)ethyl]-1,3,4-thiadiazol-2-yl]-4-hydroxy-1-methyl-2-imidazolidinone, and 3-[5-[1-(3,4-dichlorophenoxy)ethyl]-1,3,4-thiadiazol-2-yl]-4-hydroxy-1-methyl-2-imidazolidinone.

SYNTHESIS OF THE COMPOUNDS

The synthesis of the compound proceeds according to the general reactions (1), (2), (3) and (4) shown below:

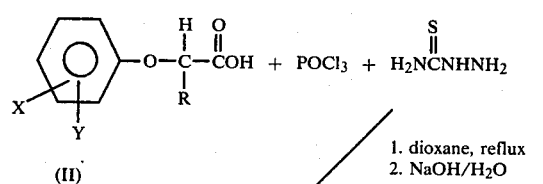

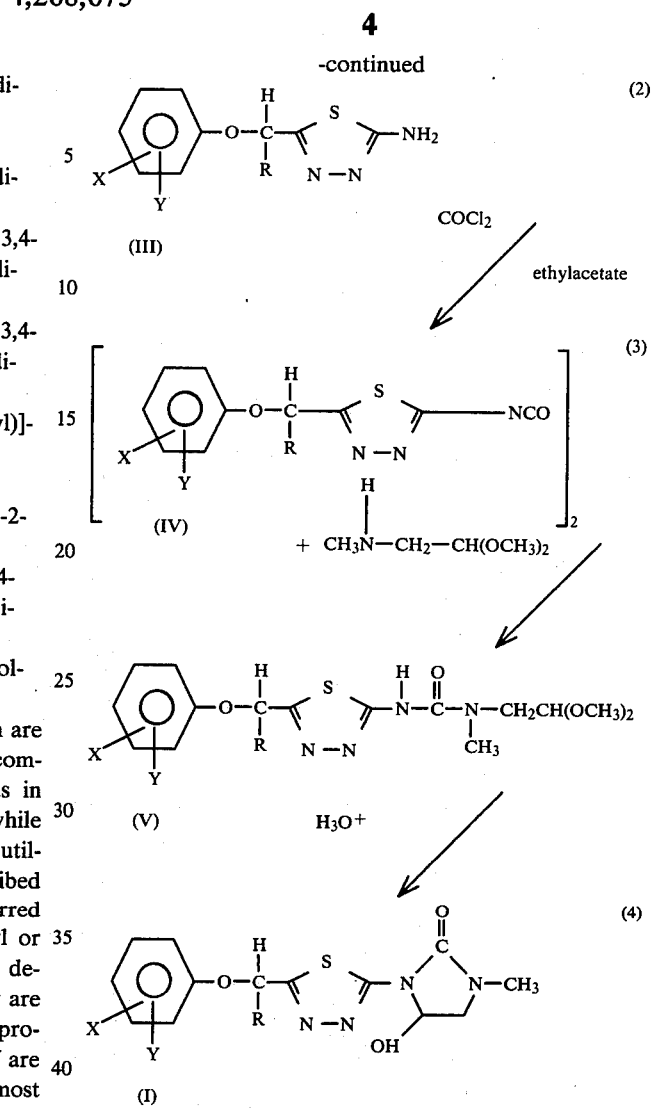

PREPARATION OF 5-SUBSTITUTED 2-AMINO-1,3,4-THIADIAZOLES

The proper alpha substituted carboxylic acid graphically represented by Formula II, wherein R and X are as described herein (typically 0.4–0.5 moles), an equimolar amount of 4-methylthiosemicarbazide, and 30 milliliters of dry dioxane, are charged into a 100 milliliter reactor equipped with a thermometer, an efficient stirrer, pressure equalized, addition funnel, and a condenser-drying tube. The addition funnel is charged with approximately 10 percent excess of phosphorus oxychloride which is added drop-wise so as to maintain a reaction temperature of 85°–95° C. and reaction occurs as shown by reaction equation 1. The mixture is then heated to reflux for about 1 hour, after which the solvent is flashed off using a vacuum such as a water aspirator. Water (50 milliliters) is added to the residue to give an emulsion which is then made basic with a 50 percent sodium hydroxide solution. In those instances that a solid product is obtained (graphically represented by Formula III, wherein X, Y, and R are as described herein), the product is isolated by filtration, and recrystallized when necessary. In other cases, the reaction mixture is extracted with ether, the ether layer is separated from the heavier layers, dried over magnesium sulfate, filtered and concentrated under vacuum to give the crude product represented as a viscous oil.

PREPARATION OF THE ISOCYANATE DIMERS

Five to 10 grams of the appropriate 2-amino-1,3,4-thiadiazole (graphically represented by Formula III) is added to a solution of phosgene in ethylacetate, (or other suitable solvent) prepared by saturating 50–100 milliliters of solvent with phosgene at room temperature then adding another 50–100 milliliters of solvent. The mixture is allowed to stir overnight at room temperature to react as shown by reaction equation 2 and then purged with nitrogen or argon to remove the unreacted phosgene. In those cases where a solid was obtained, the product (graphically represented by Formula IV, which is an isocyanate dimer of the appropriate substituted 1,3,4-thiadiazole) was isolated by filtration and dried. In cases where no solid product is evident, the reaction mixture may be topped under vacuum to give the product as a viscous oil or glass.

PREPARATION OF ACETAL UREAS

The appropriate isocyanate dimer of Formula IV and an equivalent amount of methylaminoacetaldehyde dimethylacetal were heated to reflux (5–15 minutes) in an inert solvent such as ether, benzene, or toluene, and the reaction proceeded as shown by reaction equation 3 so as to form the product graphically represented by Formula V. Some products may be produced as crystals directly from solution, but others may be induced by the addition of hexane. The product represented by graphic Formula V may be purified such as by washing with ether, or hexane or recrystallized from hexane/benzene or from ether/benzene, or from ether/chloroform/benzene solutions. Those products or compounds that are represented by Formula V obtained as oils need not be purified.

PREPARATION OF THE COMPOUNDS OF FORMULA I

The appropriate acetal urea of Formula V (approximately 3 to 4 grams) is added to 150–200 milliliters of water containing 1.5–2 milliliters of concentrated hydrochloric acid. The mixture is stirred vigorously and heated to reflux, and reaction proceeds as shown by reaction equation 4.

The hydrolysis is monitored by thin layer chromatography (alumina-ethyl acetate) until complete, and the product containing a compound of Formula I forms. The product, in some cases, may be crystallized directly from the reaction mixture upon cooling. In other cases, the compounds of Formula I are extracted with chloroform and isolated by stripping the solvent under vacuum. Those compounds which solidify upon concentration are further purified. In some cases, the compounds may be used directly as obtained. In other cases, crystallization is induced by seeding an ether solution with a related compound, and the crystals formed may be further purified.

The following examples illustrate the synthesis of the compounds described herein.

EXAMPLE I

Synthesis of 3-[5-[1-(2,4-dichlorophenoxy)ethyl]-1,3,4-thiadiazol-2-yl]-4-hydroxy-1-methyl-2-imidazolidinone a. Formation of 5-[1-(2,4-dichlorophenoxy)ethyl]-2-amino-1,3,4-thiadiazole

A 250 milliliter, 3-neck flask adapted with a Claisen adaptor, paddle stirrer, thermometer, an addition funnel and condenser, was charged with 28.2 grams (0.120 mole) of 2-(2,4-dichlorophenoxy)propanoic acid, (10.9 grams, 0.120 mole) of thiosemicarbazide and 90 milliliters of dioxane. The slurry was heated to 90° C. and the addition funnel was charged with phosphorous oxychloride ($POCl_3$). The $POCl_3$ (20.2 grams, 0.13 mole) was slowly added (for 38 minutes) while maintaining the temperature within 90°–95° C. The resulting mixture was refluxed for 115 minutes, and then evacuated by using a water aspirator to remove volatiles (HCl, $POCl_3$ and some dioxane). One hundred (100) milliliters of water was added and 50 percent NaOH solution was also added until the pH of the solution was 10. An oil formed, which was extracted with a mixture of $CH_2Cl_2$, $CHCl_3$ and diethyl ether, and the organic phase was dried over anhydrous $MgSO_4$, filtered and topped on a roto-vac at 70° C. to a greyسludge. Upon addition of diethylether, a first crop of crystals formed which were removed by filtration and then dried in a vacuum oven at 80° C. to crystals containing 5-[1-(2,4-dichlorophenoxy)ethyl-2-amino-1,3,4-thiadiazole (9.7 grams). Addition of hexane to the filtrate produced a second crop of crystals which were filtered off, dried in a vacuum oven at 80° C. to 10.1 grams of crystals. The first and second crop of crystals were combined, and recrystallized from the minimum amount of an ethanol water mixture, suction filtered, and dried in a vacuum oven at 80° C. to 17.1 grams of a grey powder of 5-[1-(2,4-dichlorophenoxy)ethyl]-2-amino-1,3,4-thiadiazole. (Melting point 119°–123° C.).

b. Formation of 5-[1-(2,4-dichlorophenoxy)ethyl]-1,3,4-thiadiazol-2-yl isocyanate dimer A 500 milliliter, neck flask equipped with a magnetic stirrer, thermometer, dry ice condenser/drying tube and inlet from a phosgene ($COCl_2$) tank via a calibrated rotameter was charged with 50 milliliters of ethyl acetate saturated with phosgene at 20° C. (approximately 0.5 mole of phosgene). An additional 100 milliliters of ethylacetate was added and 10.0 grams of 5-[1-(2,4-dichlorophenoxy)ethyl]-2-amino-1,3,4-thiadiazole, (prepared above) was added. The resulting emulsion was stirred for 17 hours; and the flask was purged with nitrogen until no $COCl_2$ was detected and a suspension formed. The solid was removed by filtration and dried in a vacuum oven at 80° C. to 5.9 grams of white crystals of 5-[1-(2,4-dichlorophenoxy)ethyl]-1,3,4-thiadiazol-2-yl isocyanate dimer. (Melting point 176°–179° C.).

c. Formation of 3-[5-[1-(2,4-dichlorophenoxy)ethyl]-1,3,4-thiadiazol-2-yl]-1-methyl-1-(2,2-dimethoxyethyl)urea A 200 milliliter flask was charged with 2.1 grams (0.018 mole) of methylaminoacetaldehyde dimethylacetal, 50 milliliters of benzene and 5.8 grams (0.018 mole)

of the 5-[1-(2,4-dichlorophenoxy)ethyl]-1,3,4-thiadiazol-2-yl isocyanate dimer (prepared above). The resulting slurry was refluxed for 15 minutes to form a yellow solution and cooled with formation of a few crystals. A minimum amount of hexane-diethylether was added, and crystallization occurred. The crystals were filtered off, and dried in a vacuum oven at 80°0 C. to give 6.4 grams of white crystals of 3-[5-[1-(2,4-dichlorophenoxy)-ethyl]-1,3,4-thiadiazol-2-yl]-1-methyl-1-(2,2-dimethoxyethyl)urea. (Melting point 125°–127° C.).

d. Synthesis of 3-[5-[1-(2,4-dichlorophenoxy)ethyl]-1,3,4-thiadiazol-2-yl]-methyl-4-hydroxy-2-imidazolidinone A solution containing 3.0 grams of the 3-[5-[1-(2,4-dichlorophenoxy)ethyl]-1,3,4-thiadiazol-2-yl]-1-methyl-1-(2,2-dimethoxyethyl)urea (prepared above) in 150 milliliters of water and 1.5 milliliters of concentrated hydrochloric acid (HCl) was refluxed for 120 minutes, cooled, the tacky goo was dissolved in chloroform, and the phases separated. The organic phase was dried over anhydrous $MgSO_4$, filtered, and azeotroped off, topped on a roto-vac at 70° C. to yield 4.4 grams of a colorless oil. The colorless oil was dissoved in 20 milliliters diethylether, seeded to form white crystals, and after the solution and crystals stood for 16 hours the crystals were removed by suction filter and air dried to yield 2.4 grams of white crystals containing 3-[5-[1-(2,4-dichlorophenoxy)ethyl]-1,3,4-thiadiazol-2-yl]-1-methyl-4-hydroxy-2-imidazolidinone with a (Melting point 132°–136° C.) and.

IR spectra (mull): C=O band at 1718 $cm^{-1}$; broad OH band at 3300 $cm^{-1}$.

NMR (DMF $d_7$): 7.55$\delta$ (mult. 1H9, 7.38$\delta$ (mult., 3H), 7.24$\delta$ (broad sing., 3H), 6.07$\delta$ (mult., 2H), 6.03$\delta$ (quartet, 2H), 3.90$\delta$ (doublet of doublets, 10-1H), 3.41$\delta$ (mult., 1H), 2.93$\delta$ (sing., 3H), 1.83$\delta$ (doublet, 3H).

EXAMPLE II

Synthesis of 3-[5-[1-(3,5-dichlorophenoxy)ethyl]-1,3,4-thiadiazol-2-yl]-4-hydroxy-1-methyl-2-imidazolidinone a. Formation of 5-[1-(3,5-dichlorophenoxy)ethyl]-2-amino-1,3,4-thiadiazole

A 100 milliliter, 3-neck flask adapted with a Claisen adaptor, paddle stirrer, thermometer, an addition funnel and condenser, was charged with 9.4 grams (0.040 mole) of 2-(3,5-dichlorophenoxy)propanoic acid, (3.6 grams, 0.040 mole) of thiosemicarbazide and 30 milliliters of dioxane. The slurry was heated to 90° C. and the addition funnel was charged with phosphorous oxychloride ($POCl_3$). The $POCl_3$ (6.7 grams, 0.044 mole) was slowly added (for 22 minutes) while maintaining the temperature within 85°–90° C. The resulting mixture was refluxed for 60 minutes. The flask was evacuated by using a water aspirator to remove volatiles (HCl, $POCl_3$ and some dioxane), fifty (50) milliliters of water was added and 50 percent solution of NaOH was also added until the pH of the solution was 10; an oil formed. The oil was extracted with diethylether, dried over $MgSO_4$, filtered, and topped in a roto-vac at 70° C. to yield 7.9 grams of a pale yellow oil of 5-[1-(3,5-dichlorophenoxy)ethyl]-2-amino-1,3,4-thiadiazol.

b. Formation of 5-[1-(3,5-dichlorophenoxy)ethyl]-1,3,4-thiadiazol-2-yl isocyanate dimer A 500 milliliter, 3-neck flask equipped with a magnetic stirrer, thermometer, dry ice condenser/drying tube and inlet from a phosgene ($COCl_2$) tank via a calibrated rotameter was charged with 50 milliliters of ethyl acetate saturated with phosgene at 20° C. (approximately 0.5 mole of phosgene). An additional 50 milliliters of ethylacetate was added, and 7.9 grams of 5-[1-(3,5-dichlorophenoxy)ethyl]-2-amino-1,3,4-thiadiazole, (prepared above) in 30 milliliters of ethyl acetate was added. The resulting solution was stirred for 64 hours, and then purged with nitrogen until no $COCl_2$ was detected. The solution was filtered and then topped at 70° C. in a roto-vac to form 10.0 grams of a viscous yellow oil of 5-[1-(3,5-dichlorophenoxy)ethyl]-1,3,4-thiadiazol-2-yl isocyanate dimer.

c. Formation of 3-[5-[1-(3,5-dichlorophenoxy)ethyl]-1,3,4-thiadiazol-2-yl]-1-methyl-1-(2,2-dimethoxyethyl)urea 3.8 grams (0.032 mole) of methylaminoacetaldehyde dimethylacetal was added to a 50 milliliter benzene solution containing 10.0 grams (0.032 mole) of the 5-[1-(3,5-dichlorophenoxy)ethyl]-1,3,4-thiadiazol-2-yl isocyanate dimer (prepared above). The resulting solution was heated to reflux, 50 milliliters of hexane was added, and the solution cooled. The crystals were filtered off, and dried in a vacuum oven at 80° C. to give 7.9 grams of fluffy waxy crystals of 3-[5-[1-(3,5-dichlorophenoxy)ethyl]-1,3,4-thiadiazol-2-yl]-1-methyl-1-(2,2-dimethoxyethyl)urea. (Melting point 149°–152° C.).

d. Formation of 3-[5-[1-(3,5-dichlorophenoxy)ethyl]-1,3,4-thiadiazol-2-yl]-1-methyl-4-hydroxy-2-imidazolidinone A solution containing 4.0 grams of the 3-[5-[1-(3,5-dichlorophenoxy)ethyl]-1,3,4-thiadiazol-2-yl-1-methyl-(2,2-dimethoxyethyl)urea (prepared above) in 200 milliliters of water and 2.0 milliliters of concentrated hydrochloric acid (HCl) was refluxed for 40 minutes. $CHCl_3$ was added to dissolve the organic material and phase separated. The organic phase was dried over $MgSO_4$, filtered and topped in a roto-vac at 70° C. to yield 4.5 grams of a yellow oil. The yellow oil was dissolved in the minimum amount of diethylether, and the solution crystallized. The crystals were removed by suction filter and the filtrate was dried over $MgSO_4$ and topped in a roto-vac at 70° C. to yield 1.3 grams of an oil containing 3-[5-[1-(3,5-dichlorophenoxy)ethyl]-1,3,4-thiadiazol-2-yl]-1-methyl-4-hydroxy-2-imidazolidinone. Diethyl ether was added, but the solution upon standing did not form crystals. The diethylether was removed by vacuum filtration, to yield 1.3 grams of a glassy residue of 3-[5-[1-(3,5-dichlorophenoxy)ethyl]-1,3,4-thiadiazol-2-yl]-1-methyl-4-hydroxy-2-imidazolidinone with an IR spectra (mull): C=O band at 1725 $cm^{-1}$, OH band at 3300 $cm^{-1}$.

EXAMPLE III

Synthesis of 3-[5-[1-(3,4-dichlorophenoxy)ethyl]-1,3,4-thiadiazol-2-yl]-4-hydroxy-1-methyl-2-imidazolidinone a. Formation of 5-[1-(3,4-dichlorophenoxy)ethyl]-2-amino-1,3,4-thiadiazole

A 100 milliliter, 3-neck flask adapted with a Claisen adaptor, paddle stirrer, thermometer, an addition funnel and condenser, was charged with 9.4 grams (0.040 mole) of 2-(3,4-dichlorophenoxy)propanoic acid, (3.6 grams, 0.040 mole) of thiosemicarbazide and 30 milliliters of dioxane and heated to 90° C. The addition funnel was charged with phosphorous oxychloride ($POCl_3$), (6.7 grams, 0.044 mole) which was slowly added (for 15 minutes) while maintaining the temperature within 85°–90° C. The resulting mixture was refluxed for approximately 100 minutes, and then topped with a water aspirator to remove volatiles (HCl, $POCl_3$ and some dioxane). Fifty (50) milliliters of water was added and 50 percent solution of NaOH was also added until the pH of the solution was 10; a solid precipitate formed. The solid precipitate was filtered off and partially air dried, and was recrystallized from the minimum amount of $H_2O$/ethanol mixture, filtered and then dried in a vacuum oven at 80° C. to 8.0 grams of fluffy white crystals of 5-[1-(3,4-dichlorophenoxy)ethyl]-2amino-1,3,4-thiadiazole. (Melting point 136°–138° C.).

b. Formation of 5-[1-(3,4-dichlorophenoxy)ethyl]-1,3,4-thiadiazol-2-yl isocyanate dimer A 500 milliliter, neck flask equipped with a magnetic stirrer, thermometer, dry ice condenser/drying tube and inlet from a phosgene ($COCl_2$) tank via a calibrated rotometer was charged with 50 milliliters of ethylacetate saturated with phosgene at 20° C. (approximately 0.5 mole of phosgene). An additional 50 milliliters of ethylacetate was added and 8.0 grams of 5-[1-(3,4-dichlorophenoxy)ethyl]-2-amino-1,3,4-thiadiazole, (prepared above) was added. The resulting solution was stirred for 17 hours with formation of an emulsion, and then purged with nitrogen until no $COCl_2$ was detected. The solution was filtered, and topped at 70° C. in a roto-vac to form 9.0 grams of a viscous yellow oil of 5-[1-(3,4-dichlorophenoxy)ethyl]-1,3,4-thiadiazol-2-yl isocyanate dimer.

c. Formation of 3-[5-[1-(3,4-dichlorophenoxy)ethyl]-1,3,4-thiadiazol-2-yl]-1-methyl-1-(2,2-dimethoxyethyl)urea 3.3 grams (0.028 mole) of methylaminoacetaldehyde dimethylacetal was slowly added to a 50 milliliter benzene solution containing 9.0 grams (0.028 mole) of the 5-[1-(3,4-dichlorophenoxy)ethyl]-1,3,4-thiadiazol-2-yl isocyanate dimer (prepared above). The resulting solution was heated to reflux and hexane was added, crystals formed on cooling. The crystals were filtered off, and dried in a vacuum oven at 80° C. to give 8.3 grams of fluffy white crystals at 3-[5-[1-(3,4-dichlorophenoxy)ethyl]-1,3,4-thiadiazol-1-yl]-1-methyl-1-(2,2-dimethoxyethyl)urea. (Melting point 124°–127° C.).

d. Synthesis of 3-[5-[1-(3,4-dichlorophenoxy)ethyl]-1,3,4-thiadiazol-2-yl]-1-methyl-4-hydroxy-2-imidazolidinone A solution containing 4.0 grams of the 3-[5-[1-(3,4-dichlorophenoxy)ethyl]-1,3,4-thiadiazol-2-yl]-1-methyl-(2,2-dimethoxyethyl)urea (prepared above) in 200 milliliters of water and 2 milliliters of concentrated hydrochloric acid (HCl) was refluxed for 165 minutes, cooled and then extracted with chloroform $CHCl_3$, and phase separated. The organic phase was dried over $MgSO_4$, filtered, and topped in a roto-vac at 70° C. to yield 3.9 grams of a viscous oil. The viscous oil was dissolved in 20 milliliters of diethylether, and the solution crystallized. The crystals were removed by suction filter, and were dried in a vacuum oven at 80° C. to yield 1.9 grams of white crystals of 3-[5-[1-(3,4-dichlorophenoxy)ethyl]-1,3,4-thiadiazol-2-yl]-1-methyl-4-hydroxy-2-imidazolidinone with a (Melting point 135°–138° C.) and IR spectra (neat): C=O band at 1720 $cm^{-1}$, broad OH band at 3200 $cm^{-1}$.

INTERMEDIATE COMPOUNDS

The other compounds described herein and represented graphically by Formulas III, IV and V possess some herbicidal control, and these compounds are very useful intermediates in the synthesis of the novel compounds represented by Formula I.

APPLICATIONS OF THE COMPOSITIONS AGAINST WEEDS

The novel active compounds of Formula I are particularly valuable for weed control because they are toxic to many species and groups of weeds and are relatively non-toxic to many beneficial plants. The exact amount of one or more of the compounds required depends upon a variety of factors, including the hardiness of the particular weed species, the weather, the type of soil, the method of application, the kind of beneficial plants in the same area and the like. Thus, while the application of up to only about 1 or 2 ounces of active compound per acre may be sufficient for good control of a light infestation of weeds growing under adverse conditions, the application of 8 pounds or 10 pounds or more of an active compound of Formula I per acre may be required for good control of a dense infestation of hardy perennial weeds growing under favorable conditions.

a. Examples Of Weeds Which May Be Controlled By The Compounds Described Herein Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds. It is believed that the compositions set forth herein, when applied in a herbicidally effective amount may control field pennycress, ryegrass, goosegrass, chickweed, purslane, smartweed, knotweed, wild buckwheat, kochia, medic, corn cockle, ragweed, sowthistle, croton, cuphea, dodder, fumitory, groundsel, hempnettle, knawel, spurge, spurry emex, jungle rice, pondweed, dogfennel, carpetweed, bedstraw, ducksalad, naiad, chestgrass, fall panicum, witchgrass, switchgrass, watergrass, teaweed, wild turnip and springletop; biennials such as wild carrot, matricaria, wild barley, campion, chamomile, burdock, mullein, round-leaved mallow, bull thistle, houndstongue, moth mullein, and purple star thistle; or perennials such as white cockle, perennial ryegrass, quackgrass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania bulrush, cat-tail, winter-cress, horsenettle, nutsedge, milkweed and sicklepod.

The important weeds of the genera against which the compounds having X and Y as chlorine at the 3, 4 position of the invention are most effective preemergence at 10 pounds per acre are: Datura, Digitaria, Abutilon and Ipomoea. Weed species against which these compounds are most effective preemergence are: *Datura stramonium* (jimsonweed), *Digitaria sanguinalis* (L) (crabgrass, large), *Abutilon theophrasti* (L), (velvetleaf) and *Ipomoea purpurea* (L) Roth (tall morningglory).

Important weeds of the genera against which the compounds having X and Y as chlorine at the 3, 5 positions are most effective preemergence at 10 pounds per acre are: Sida, Datura, Brassica, Setaria, Sorghum, Digitaria, Ipomoea and Avena. Weed species against which the compounds of the invention are most effective preemergence are: *Sida spinosa* (L) (teaweed), *Datura stramonium* (jimsonweed), *Brassica kaber* (wild mustard), *Sorghum halepense* (johnsongrass), *Setaria glauca* (L) (yellow foxtail), *Ipomoea purpurea* (L) Roth (tall morningglory), *Avena fatua* (wild oats), and *Digitaria sanguinalis* (L) (crabgrass, large).

Important weeds of the genera against which the compounds having X and Y as chlorine at the 2, 4 positions are most effective preemergence at 10 pounds per acre are: Datura, Brassica, Setaria, Sorghum, Sesbania, Digitaria, Ipomoea and Avena. Weed species against which the compounds of the invention are most effective preemergence are: *Datura stramonium* (jimsonweed), *Brassica kaber* (wild mustard), *Sorghum halepense* (johnsongrass), *Setaria glauca* (L) (yellow foxtail), *Sesbania spp.* (coffeeweed), *Digitaria sanguinalis* (L) (crabgrass, large), *Ipomoea purpurea* (L) Roth (tall morning-glory) and *Avena fatua* (wild oats).

b. Description Of The Method Of Controlling Weeds

As used herein and in the Claims, the method of controlling the weeds comprises contacting the weeds with a herbicidally effective amount of a compound represented by the graphic formula described herein. The term "contacting the weeds" refers to any method of contacting the weeds, both preemergence (before the weeds appear) and/or postemergence (after the weeds appear), such as applying granules of the compound to the soil prior to emergence, or spraying a solution of the compound or compounds described by the general formula, or any other method known in the art by which the weeds are contacted either before they emerge of after they emerge, or both before and after they emerge, with one or more of the compounds represented by the general Formula I described herein. But, preferably the weeds are contacted preemergence with the compounds of Formula I. The phrase "herbicidally effective amount" refers to that amount required under the environmental conditions in order to effectively control, that is, by which the weeds are injured so as not to be able to recover from the application of the compound, or to be killed by the compound.

c. General Application Of The Compounds

For practical use as herbicides, the compounds of this invention are generally incorporated into herbicidal formulations which comprise an inert carrier and a herbicidally toxic amount of a compound mentioned herein. Such herbicidal formulations enable the active compound to be applied conveniently to the site of the weed infestation in any desired quantity. These formulations can be solids such as dusts, granules, or wettable powders or they can be liquids such as solutions, aerosols or emulsifiable concentrates.

For example, dusts can be prepared by grinding and blending the active compound with a solid inert carrier such as the talcs, clays, silicas, prophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust composition.

In some cases, the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems, an inverted emulsion (water in oil) can be prepared for direct application to weed infestations.

A typical herbicidal formulation according to this invention is illustrated by the following example, in which the quantities are in parts by weight.

EXAMPLE IV

Preparation Of A Dust

Product of Example I: 10
Powdered Talc: 90

The above ingredients are mixed in a mechanical grinder-blender and are ground until a homogeneous, freeflowing dust of the desired particle size is obtained. This dust is suitable for direct application to the site of the weed infestation.

d. Mixtures Of Compounds Alone Or In Mixtures

Although all of the compounds described herein and represented by the general formula described herein are useful as herbicides, some of these are preferred and are better for application against weeds. In general, all of the compounds described herein may be used either alone or together in mixtures. When used in mixtures, the amount or ratio of one compound to another may vary from 0.01 to 100.

e. Manner Of Application Of The Compounds Of This Invention

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulations and will comprise from about 0.05 to about 95 percent by weight of the active compounds of this invention. In a preferred embodiment of this invention, the herbicidal formulations can also comprise other pesticides, such as insecticides, nematocides, fungicides and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provides herbicidal formulations which are re effective in controlling weeds and often provide results unattainable with separate formulations of the individual herbicides.

f. Examples of Other Pesticides and Herbicides For Combinations

The other herbicides, defoliants, desiccants, and plant growth inhibitors, with which the compounds of this invention can be used in the herbicidal formulations to control weeds, can include chlorophenoxy herbicides such as: 2,4,-D, 2,4,5-T, MCPA, MCPB, 4-(2,4-DB), 2,4-DEB, 4-CPB, 4-CPA, 5-CPP, 2,4,5-TES, 3,4-DA silvex and the like; carbamate herbicides such as IPC, CIPC, swep, barban, BCPC, CEPC, CPPC and the like; thiocarbamate and dithiocarbamate herbicides such as: CDEC, metam sodium, EPTC, diallate, PEBC, perbulate, vernolate and the like; substituted urea herbicides such as: norea, siduron, dichloroal urea, chloroxuron cycluron, fenuron, monuron, monuron TCA, diuron, linuron, monolinuron, neburon, buturon, trimeturon and the like; symmetrical triazine herbicides such as: simazine, chlorazine, atraone, desmetryne, norazine, ipazine, prometryn, atrazine, trietazine, simetone, prometone, propazine, ametryne and the like; chloroacetamide herbicides such as: alpha-chloro-N,N-dimethylacetamide, CDEA, CDAA, alphachloro-N-isopropyl-acemide, 2-chloro-N-isopropylacetanilide, 4-(chloroacetyl) morpholine, 1-(chloroacetyl) piperidine and the like; chlorinated aliphatic acid herbicides such as: TCA, dalapon, 2,3-dichloropropionic acid, 2,2,3-TPA, and the like; chlorinated benzoic acid and phenylacetic acid herbicides such as: 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,5-dichloro-3-nitrobenzoic acid, dual, metribuzin and the like; and such compounds as aminotriazole, maleic hydrazode, phenyl mercuric acetate, endothall, biuret, technical chlordane, dimethyl 2,3,5,6-tetrachlorotetephthalate, diquat, erbon, DNC, DNBP, dichlorobenil, CPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dine, bromoxynil, cacodylic acid, CMA, CPMF, cypromid, DCB, DCPA, dichlone, diphenatril, DMITT, DNAP, EXD, ioxynil, isocil, potassium cyanate, MAA, MAMA, MCPES, MCPP, MH, molinate, NPA, paraquat, PCP, picloram, DPA, PCA, pyrichlor, sesone, terbacil, terbutol, TCBA, LASSO, planavin, sodium tetraborate, calcium cyanamide, DEF, ethyl xanthogen disulfide, sindone, sindone B, propanil and the like. Such herbicides can also be used with the compositions of this invention in the form of their salts, esters, amides, and other derivatives whenever applicable to the particular parent compounds.

g. Examples of Herbicidal Control

The following examples illustrate the method of controlling the weeds described herein. These examples were conducted under standard laboratory conditions, using standard laboratory procedures.

EXAMPLE V

When the compound of 3-[5-[1-(3,5-dichlorophenoxy)ethyl]-1,3,4-thiadiazol-2-yl]-4-hydroxy-1-methyl-2-imidazolidinone (Example II) was applied preemergence at 10 pounds per acre to the weed species: *Sida spinosa* (teaweed), *Datura stramonium* (L) (jimsonweed), *Ipomoea purpurea* (L) Roth (morningglory), *Avena fatua* (L) (wild oats), *Abutilon theophrasti* (L) (velvetleaf), *Sorghum halepense* (L), (johnsongrass), *Digitaria sanguinalis* (L) (crabgrass), *Setaria glauca* (L) (yellow foxtail) and *Brassica kaber* (L) (wild mustard), at the end of 21 days many of the weeds were so severely injured that they could not recover, and others were killed.

EXAMPLE VI

When the compound of 3-[5-[1-(2,4-dichlorophenoxy)ethyl]-1,3,4-thiadiazol-2-yl]-4-hydroxy-1-methyl-2-imidazoidinone (Example I) was applied preemergence at 10 pounds per acre to the weed species: *Brassica kaber* (L) (wild mustard), *Sesbania spp.* (coffeeweed), *Ipomoea purpurea* (L) Roth (morningglory), *Avena fatua* (L) (wild oats), *Sorghum halepense* (L) (johnsongrass), *Digitaria sanguinalis* (L) (crabgrass), *Setaria glauca* (L) (yellow foxtail) and *Datura stramonium* (L) (jimsonweed), at the end of 21 days many of the weeds were so severely injured that they could not recover, and others were killed.

EXAMPLE VII

When the compound of 3-[5-[1-(3,4-dichlorophenoxy)ethyl]-1,3,4-thiadiazol-2-yl]-4-hydroxy-1-methyl-2-imidazolidinone (Example III) was applied preemergence at 10 pounds per acre to the weed species: *Datura stramonium* (L) (jimsonweed), *Ipomoea purpurea* (L) Roth (morningglory), *Abutilin theophrasti* (L) (velvetleaf) and *Digitaria sanguinalis* (L) (crab-grass), at the end of 21 days many of the weeds were so severely injured that they could not recover and others were killed.

EXAMPLE VIII

When the compound 3-[5-(2,4-dichlorophenoxymethyl)-1,3,4-thiadiazol-2-yl]-4-hydroxy-1-methyl-2-imidazolidinone, which was prepared in a manner similar to that of the compound of Example I was applied to the same weed species and under the same conditions as in Example VI, all of the weed species were growing.

While the invention has been described with reference to the specific details of certain illustrative embodiments, it is not intended that it shall be limited thereby except so far as such details appear in the accompanying claims.

I claim:
1. A compound graphically represented by Formula I

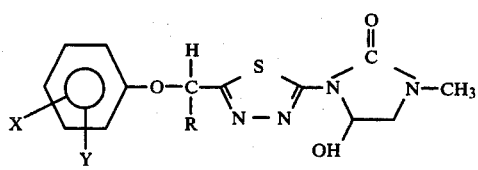

wherein:
X is chlorine, bromine, fluorine, or iodine
Y is chlorine, bromine, fluorine, or iodine, and R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 2-bromoethyl.

2. The compound as recited in claim 1 wherein R is an alkynyl of up to three carbon atoms.

3. The compound as recited in claim 1 wherein R is an alkenyl of up to three carbon atoms.

4. The compound as recited in claim 1 wherein R is a haloalkyl selected from the group consisting of chloromethyl, bromomethyl, 2-chloroethyl, and 2-bromoethyl.

5. The compound as recited in claim 1 wherein R is a haloalkyl selected from the group consisting of chloromethyl and bromomethyl.

6. The compound as recited in claim 1 wherein R is an alkyl of up to four carbon atoms.

7. The compound as recited in claim 1 wherein R is an alkyl selected from the group consisting of methyl, ethyl, and propyl.

8. The compound as recited in claim 1 wherein R is methyl.

9. The compound as recited in claim 1, 2, 3, 4, 5, 6, 7, or 8 wherein X is at the two (2) position and Y is at the four (4) position.

10. The compound as recited in claim 1, 2, 3, 4, 5, 6, 7, or 8 wherein X is at the three (3) position and Y is at the four (4) position.

11. The compound as recited in claims 1, 2, 3, 4, 5, 6, 7, or 8 wherein X is at the three (3) position and Y is at the five (5) position.

12. The compound as recited in claim 9 wherein X and Y are bromine.

13. The compound as recited in claim 10 wherein X and Y are bromine.

14. The compound as recited in claim 11 wherein X and Y are bromine.

15. The compound as recited in claim 9 wherein X and Y are chlorine.

16. The compound as recited in claim 10 wherein X and Y are chlorine.

17. The compound as recited in claim 11 wherein X and Y are chlorine.

18. 3-[5-[1-(2,4-dichlorophenoxy)ethyl]-1,3,4-thiadiazol-2-yl]-4-hydroxy-1-methyl-2-imidazolidinone.

19. 3-[5-[1-(3,4-dichlorophenyl)]-1,3,4-thiadiazol-2-yl]-4-hydroxy-1-methyl-2-imidazolidinone.

20. 3-[5-[1-(3,5-dichlorophenoxy)ethyl]-1,3,4-thiadiazol-2-yl]-4-hydroxy-1-methyl-2-imidazolidinone.

* * * * *

UNITED STATES PATENT AND TRADEMARK OFFICE
CERTIFICATE OF CORRECTION

PATENT NO. : 4,268,675
DATED : May 19, 1981
INVENTOR(S) : Jerome M. Lavanish

It is certified that error appears in the above-identified patent and that said Letters Patent are hereby corrected as shown below:

In Claim 19, column 16, line 34, that portion of the named compound reading "[1-(3,4-dichlorophenyl)]" should read --[1-(3,4-dichlorophenoxy)ethyl]--.

*Signed and Sealed this*

*Eighteenth* Day of *August 1981*

[SEAL]

Attest:

Attesting Officer

GERALD J. MOSSINGHOFF

*Commissioner of Patents and Trademarks*